US010235558B2

(12) United States Patent
Klein et al.

(10) Patent No.: US 10,235,558 B2
(45) Date of Patent: *Mar. 19, 2019

(54) FINGERPRINT SENSOR-COMPATIBLE OVERLAY MATERIAL

(71) Applicant: Cypress Semiconductor Corporation, San Jose, CA (US)

(72) Inventors: Hans Klein, Pleasanton, CA (US); Igor Kolych, Lviv (UA); Oleksandr Karpin, Lviv (UA); Igor Kravets, Lviv (UA); Oleksandr Hoshtanar, Lviv (UA)

(73) Assignee: Cypress Semiconductor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/472,473

(22) Filed: Mar. 29, 2017

(65) Prior Publication Data

US 2017/0262685 A1 Sep. 14, 2017

Related U.S. Application Data

(63) Continuation of application No. 15/347,400, filed on Nov. 9, 2016, now Pat. No. 9,639,734.

(Continued)

(51) Int. Cl.
*G06K 9/00* (2006.01)
*A61B 18/20* (2006.01)
(Continued)

(52) U.S. Cl.
CPC .......... *G06K 9/00053* (2013.01); *A61B 18/20* (2013.01); *A61B 18/203* (2013.01);
(Continued)

(58) Field of Classification Search
CPC .... G06K 9/0002; A61B 18/20; A61B 18/203; A61B 2017/00057; A61B 2018/00452;
(Continued)

(56) References Cited

U.S. PATENT DOCUMENTS

| 6,088,471 A | 7/2000 | Setlak et al. |
| 6,512,381 B2 | 1/2003 | Kramer |

(Continued)

FOREIGN PATENT DOCUMENTS

| CN | 103425965 A | 12/2013 |
| WO | 2014207287 A1 | 12/2014 |
| WO | 2015096807 A1 | 7/2015 |

OTHER PUBLICATIONS

Ganji, Bahram Azizollah, "A High Sensitive MEMS Capacitive Fingerprint Sensor Using Slotted Membrane", Microsystem Technologies, Jan. 2013, vol. 19, Issue 1, pp. 121-129; 9 pages.

(Continued)

*Primary Examiner* — Manuchehr Rahmjoo

(57) ABSTRACT

A fingerprint sensor-compatible overlay material which uses anisotropic conductive material to enable accurate imaging of a fingerprint through an overlay is disclosed. The anisotropic conductive material has increased conductivity in a direction orthogonal to the fingerprint sensor, increasing the capacitive coupling of the fingerprint to the sensor surface, allowing the fingerprint sensor to accurately image the fingerprint through the overlay. Methods for forming a fingerprint sensor-compatible overlay are also disclosed.

14 Claims, 19 Drawing Sheets

Related U.S. Application Data

(60) Provisional application No. 62/316,451, filed on Mar. 31, 2016, provisional application No. 62/255,027, filed on Nov. 13, 2015.

(51) Int. Cl.

| | | |
|---|---|---|
| A61B 17/00 | (2006.01) | |
| A61B 18/00 | (2006.01) | |
| H01S 3/02 | (2006.01) | |
| H01S 3/092 | (2006.01) | |
| H01S 3/131 | (2006.01) | |
| H01S 3/213 | (2006.01) | |

(52) U.S. Cl.
CPC .............. *A61B 2017/00057* (2013.01); *A61B 2018/00452* (2013.01); *A61B 2018/00476* (2013.01); *H01S 3/022* (2013.01); *H01S 3/092* (2013.01); *H01S 3/1312* (2013.01); *H01S 3/213* (2013.01)

(58) Field of Classification Search
CPC ........... A61B 2018/00476; H01S 3/022; H01S 3/092; H01S 3/1312; H01S 3/213
USPC ......................................................... 382/124
See application file for complete search history.

(56) References Cited

U.S. PATENT DOCUMENTS

| | | | |
|---|---|---|---|
| 7,028,893 B2 | 4/2006 | Goodman et al. | |
| 8,410,795 B1 | 4/2013 | Peng et al. | |
| 8,803,823 B2 | 8/2014 | Chang et al. | |
| 8,964,298 B2 | 2/2015 | Haddick et al. | |
| 9,135,495 B1 | 9/2015 | Pope et al. | |
| 9,152,841 B1 | 10/2015 | Riedijk | |
| 9,158,958 B2 | 10/2015 | Wickboldt et al. | |
| 9,298,966 B2 | 3/2016 | Setlak et al. | |
| 9,389,258 B2* | 7/2016 | Kravets ................... | G06F 3/044 |
| 9,460,332 B1 | 10/2016 | Bussat | |
| 9,547,788 B1 | 1/2017 | Ogirko et al. | |
| 9,639,734 B1 | 5/2017 | Klein et al. | |
| 9,889,258 B2* | 2/2018 | Bengtsson ............... | A61M 5/24 |
| 10,061,961 B2 | 8/2018 | Ogirko et al. | |
| 2003/0107097 A1 | 6/2003 | McArthur et al. | |
| 2005/0189136 A1* | 9/2005 | Kawasaki ......... | H01L 23/49811 174/255 |
| 2008/0093687 A1 | 4/2008 | Antaki | |
| 2011/0102569 A1 | 5/2011 | Erhart | |
| 2013/0009651 A1 | 1/2013 | Benkley | |
| 2013/0093500 A1 | 4/2013 | Bruwer | |
| 2013/0265040 A1 | 10/2013 | Ide et al. | |
| 2013/0271422 A1 | 10/2013 | Hotelling et al. | |
| 2014/0063374 A1 | 3/2014 | Kuriki | |
| 2014/0085247 A1 | 3/2014 | Leung et al. | |
| 2014/0219521 A1 | 8/2014 | Schmitt et al. | |
| 2015/0036065 A1 | 2/2015 | Yousefpor et al. | |
| 2015/0071509 A1 | 3/2015 | Myers | |
| 2015/0187136 A1 | 7/2015 | Grimaud | |
| 2015/0189136 A1* | 7/2015 | Chung, II .......... | G06K 9/00013 348/77 |
| 2016/0026842 A1 | 1/2016 | Withers et al. | |
| 2016/0357316 A1 | 12/2016 | Koizumi | |

OTHER PUBLICATIONS

International Search Report for International Application No. PCT/US16/61270 dated Jan. 12, 2017; 2 pages.

Sheu, Meng-Lieh, "A CMOS Readout Circuit for LTPS-TFT Capacitive Fingerprint Sensor", IEEE Conference on Electron Devices and Solid-State Circuits 2005,DOI: 10.1109/EDSSC.2005.1635353; 5 pages.

USPTO Notice of Allowance for U.S. Appl. No. 15/347,400 dated Dec. 21, 2016; 10 pages.

Written Opinion of the International Searching Authority for International Application No. PCT/US16/61270 dated Jan. 12, 2017; 8 pages.

USPTO Examiner Initiated Interview Summary U.S. Appl. No. 15/347,400 dated Dec. 21, 2016; 1 page.

"News Briefs: Biometric Fingerprint Reader Works Through Latex Gloves," published on Jul. 1, 2011 [retrieved on Mar. 29, 2016], retrieved from internet <URL: http://www.locksmithledger.com/>.

International Search Report for International Application No. PCT/US16/61273 dated Dec. 15, 2016; 4 pages.

USPTO Non-Final Rejection for U.S. Appl. No. 15/088,479 dated Jun. 28, 2016; 18 pages.

USPTO Non-Final Rejection for U.S. Appl. No. 15/368,905 dated Feb. 8, 2018; 12 pages.

USPTO Notice of Allowance for U.S. Appl. No. 15/088,479 dated Sep. 7, 2016; 9 pages.

USPTO Notice of Allowance for U.S. Appl. No. 15/368,905 dated May 7, 2018; 15 pages.

Written Opinion of the International Searching Authority for International Application No. PCT/US16/61273 dated Dec. 15, 2016; 8 pages.

SIPO Office Action for Application No. 201680057006.X dated Nov. 5, 2018; 9 pages.

USPTO Notice of Allowance for U.S. Appl. No. 16/113,374 dated Dec. 19, 2018; 10 pages.

\* cited by examiner

FINGERPRINT SENSOR-COMPATIBLE OVERLAY MATERIAL

RELATED APPLICATION

This patent application claims the benefit of U.S. patent application Ser. No. 15/347,400, filed Nov. 9, 2016, which claims the benefit of U.S. Provisional Patent Application No. 62/316,451, filed Mar. 31, 2016, and claims the benefit of U.S. Provisional Patent Application No. 62/255,027, filed Nov. 13, 2015, all of which are incorporated by reference herein in their entirety.

TECHNICAL HELD

The present disclosure relates generally to structures and manufacturing methods of an anisotropic conductive material, and more particularly, an anisotropic conductive material which is compatible with a sensor sensing a fingerprint through the material.

BACKGROUND

Various devices and systems such as computing devices, mobile communication devices, automotive equipment, industrial equipment, home white goods, and entry systems may require an authentication method to protect against unauthorized access. Fingerprint authentication using fingerprint sensors may protect an apparatus or system against unauthorized access.

Fingerprint sensors may use various capacitive sensing methods to image a fingerprint pattern, where imaging a fingerprint means detecting fingerprint and generating a set of data values, or "fingerprint data," that represents the fingerprint in digital format. The fingerprint data may be an image or other information specific to a fingerprint. This method requires direct contact or close proximity of the portion of the finger comprising the fingerprint, or "finger pad," with the sensor surface. A very thin cover, or overlay, may be disposed over the sensor surface. Thick overlays between the fingerprint and the fingerprint sensor may obscure fingerprint features.

There may be a variety of situations when a user may want to image a fingerprint through a thick material. A user may want to image a fingerprint using a sensor which is overlayed by a thick material to protect the sensor (or the device which includes the sensor) against harmful environmental factors, such as cold and water, and harmful physical factors, such as sharp objects and corrosive chemicals, or to improve the appearance of the fingerprint sensor, such as by providing a continuous surface with a touchscreen. A protective enclosure or cover may be fabricated with rigid material, such as, but not limited to, glass or plastic, or flexible material, such as, but not limited to, fabric or film. A protective enclosure may completely enclose a device or may partially enclose a device. Current fingerprint sensors cannot image fingerprints through thick material. Using an enclosure or cover material that is thin enough to enable fingerprint sensing may limit the protective effectiveness of the enclosure or film. If using a thick enclosure or cover material, the user may have to remove the device from the enclosure or cover to enable fingerprint sensing. Removing the cover or enclosure may be inconvenient for the user and/or may risk damaging the device. It is desirable to create a material which can overlay the sensor where the material is thick enough for protection but enables accurately imaging a fingerprint through the material.

SUMMARY

In an embodiment, an anisotropic conductive material is disclosed which is thick enough for protection but enables a fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

In an embodiment, method for fabricating an anisotropic conductive material is disclosed. The anisotropic conductive material is substantially more conductive in one direction, than in other directions.

In an embodiment, a method is disclosed for imaging a fingerprint by a fingerprint sensor overlayed with an anisotropic conductive material which is thick enough to provide protection but enables the fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

In an embodiment, a fingerprint sensor apparatus is disclosed for imaging a fingerprint by a fingerprint sensor overlayed with an anisotropic conductive material which is thick enough to provide protection but enables the fingerprint sensor to accurately image a fingerprint through the material. The anisotropic conductive material is substantially more conductive in one direction, such as a direction orthogonal to the surface of a fingerprint sensor, than in other directions, increasing the capacitive coupling of the fingerprint to the sensor surface, allowing the fingerprint sensor to accurately image the fingerprint through the material.

DETAILED DESCRIPTION

Figure 1:
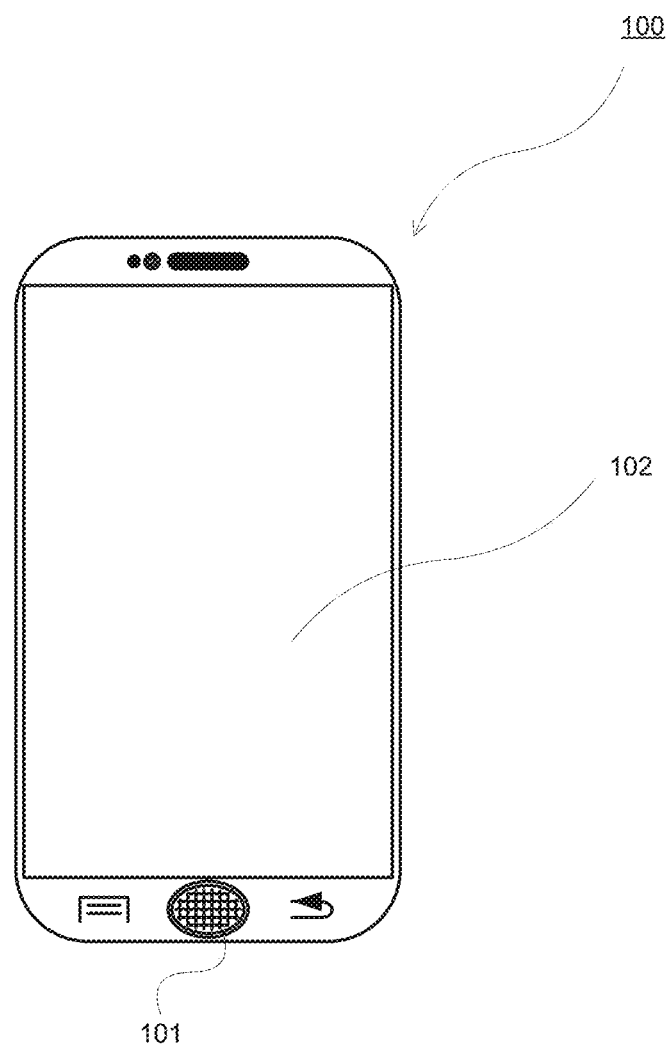
FIG. 1 illustrates a device with a fingerprint-enabled authentication system.

In the following description, for purposes of explanation, numerous specific details are set forth in order to provide a thorough understanding of the embodiments of the present invention discussed herein. It will be evident, however, to one skilled in the art that these and other embodiments may be practiced without these specific details. In other instances, well-known circuits, strictures, and techniques are not shown in detail, but rather in a block diagram in order to avoid unnecessarily obscuring an understanding of this description.

Reference in the description to "one embodiment" or "an embodiment" means that a particular feature, structure, or characteristic described in connection with the embodiment is included in at least one embodiment of the invention. The phrase "in one embodiment" located in various places in this description does not necessarily refer to the same embodiment.

For simplicity and clarity of illustration, reference numerals may be repeated among the figures to indicate corresponding or analogous elements. Numerous details are set forth to provide an understanding of the embodiments described herein. The examples may be practiced without these details. In other instances, well-known methods, procedures, and components are not described in detail to avoid obscuring the examples described. The description is not to be considered as limited to the scope of the examples described herein.

Fingerprint Sensing and Imaging

FIG. 1 illustrates an embodiment of a device 100 with a fingerprint-enabled authentication system. Device 100 may be a mobile communication device comprising a fingerprint sensor 101 which may enable user access to device applications. Surface 102 may be a display or touchscreen. Other embodiments of devices or systems system with fingerprint-enabled authentication systems may include an automotive console, an industrial control pad, a home security console, and an entry pad.

In each such device or system, a fingerprint may be imaged using a fingerprint sensor 101, where imaging a fingerprint may comprise detecting a fingerprint and generating a set of data values, or "fingerprint data," that represents the fingerprint in digital format. The fingerprint data may then be stored in a memory location. A second fingerprint may subsequently be imaged. The first set and second set of fingerprint data may be compared to determine if they share fingerprint features. Upon determining the two sets of fingerprint data share a significant number of features, the device may enable the user to access the device or system.

Figure 2:
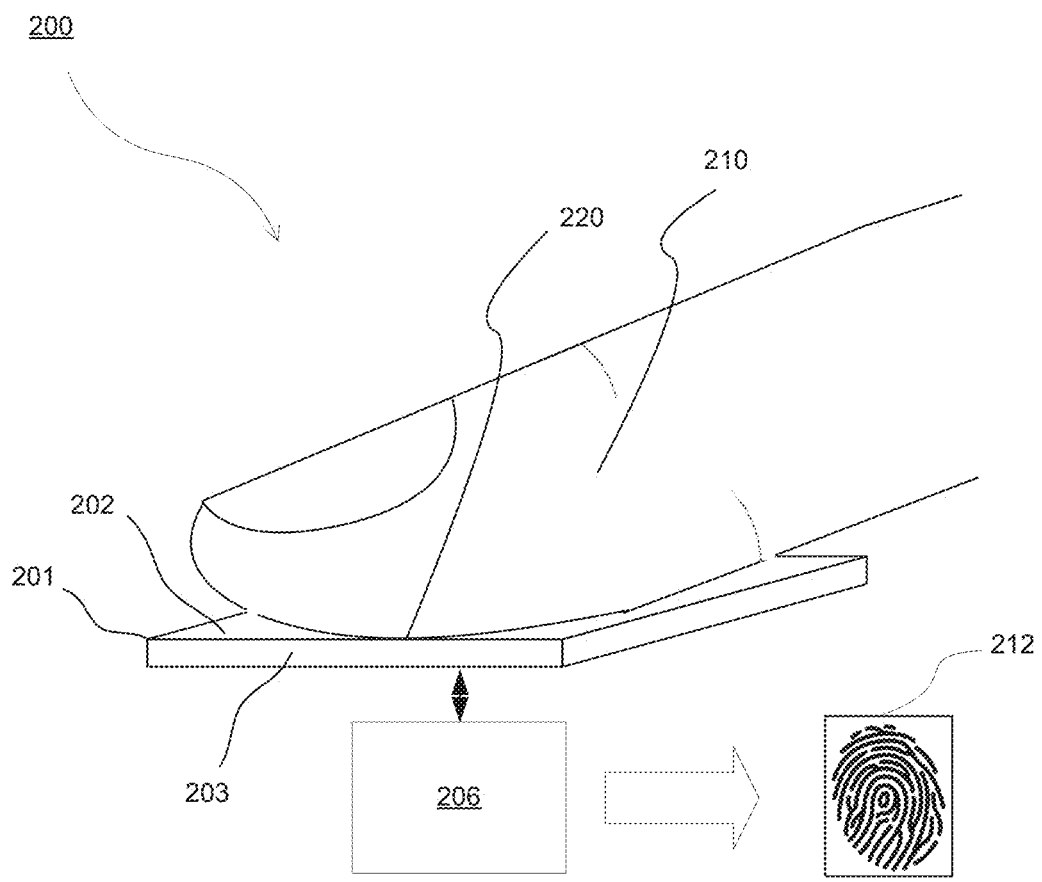
FIG. 2 illustrates a fingerprint sensing system.

FIG. 2 illustrates a fingerprint sensor 200 in accordance with various embodiments. The fingerprint sensor 200 includes a sensor surface 201. A portion of finger 210 comprising a fingerprint, or "finger pad," 220 may be disposed in direct contact with or in close proximity to sensor surface 202. Fingerprint sensor 201 comprises an array of capacitive sensors 203 (not shown). Sensor surface 202 may be disposed over array 203, which experiences changes in capacitance in response to the contact or proximity of fingerprint features of finger 210. Fingerprint sensor 201 may be coupled to processor or controller 206. Processor/controller 206 may be configured to receive voltage or current signals from capacitive sense elements 203 which correspond to measured capacitance on and/or between capacitive sense elements 203, and to convert the voltage or current signals to fingerprint data, represented by visual representation of a fingerprint 212.

Figure 3:
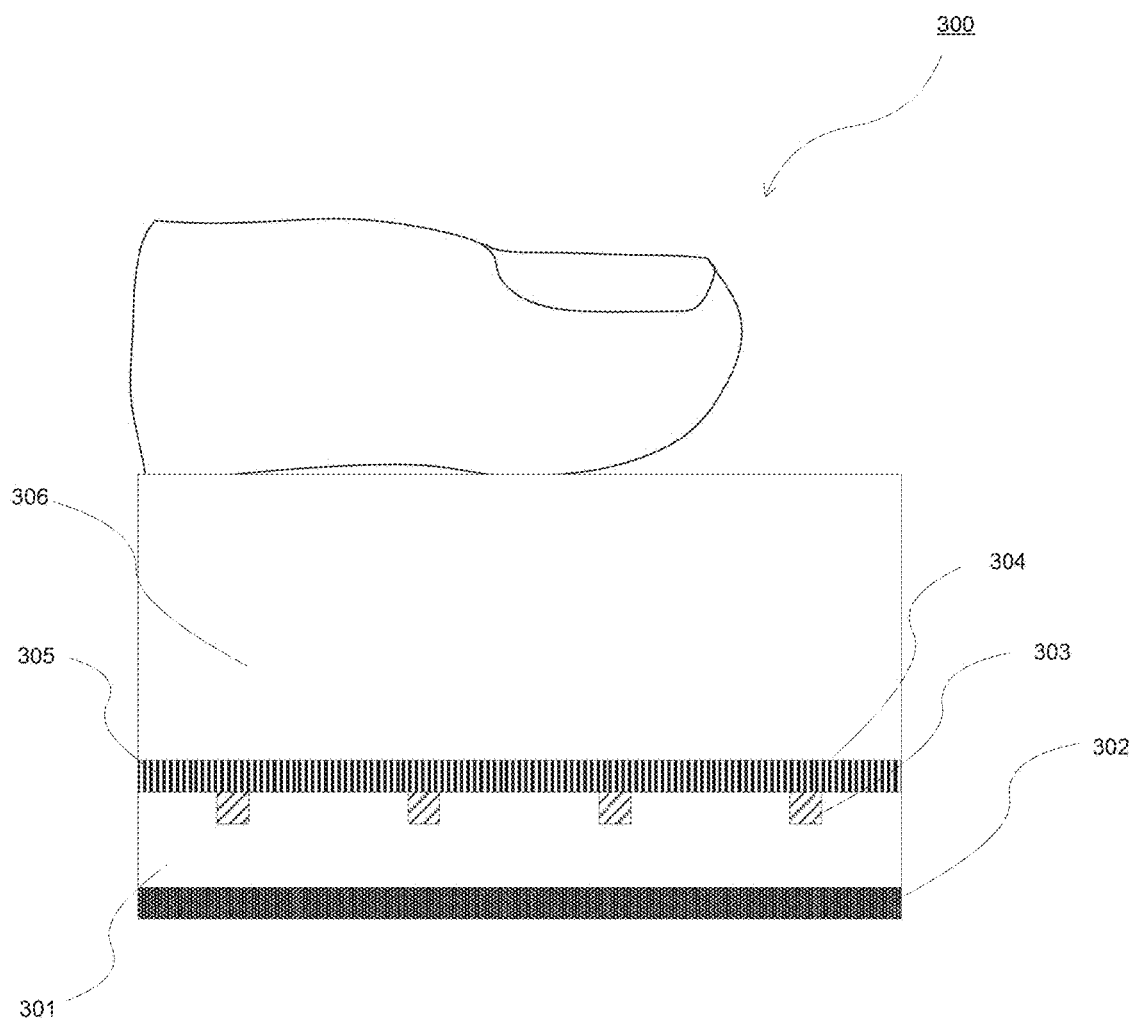
FIG. 3 illustrates a fingerprint sensor structure.

FIG. 3 illustrates a fingerprint sensor structure 300 in accordance with various embodiments. The fingerprint sensor structure 300 includes a fingerprint sensor 301, which includes a sensor array comprising Tx electrodes 302 and Rx electrodes 303, and a sensor surface 304. Fingerprint sensor structure 300 includes an overlay 306 and an intermediate layer 305, which may be glass to provide a sensor surface, or adhesive to attach overlay 306, or paint for color matching. In other embodiments there may be more than one intermediate layer between sensor surface 304 and overlay 306, or between overlay 306 and fingerprint pad 307.

Figure 4:
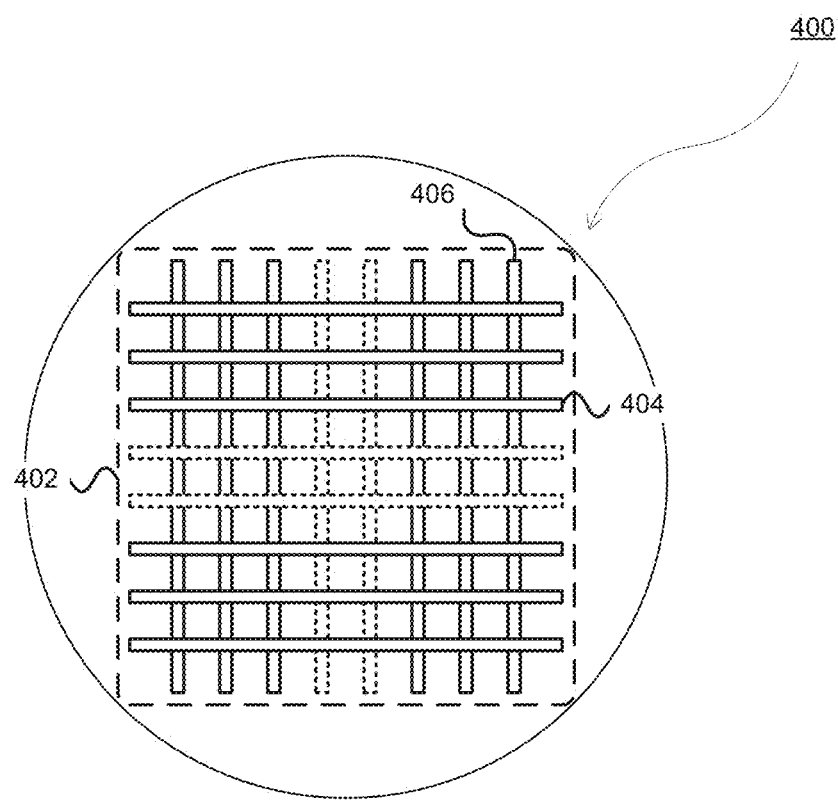
FIG. 4 illustrates a capacitive sensor array suitable for detecting and imaging fingerprints.

FIG. 4 illustrates an embodiment of a capacitive sensor array 400 suitable for detecting and imaging fingerprints. Capacitive sensor array 400 may include a number of electrodes arranged in an array 402 of row electrodes 404 in a first axis and column electrodes 406 in a second axis. FIG. 4 illustrates eight row electrodes 404 and eight column electrodes 406, but there may be considerably more electrodes disposed along both axes. Depending on the size of the array, there may be dozens or hundreds of electrodes for each row and column. The exact size and pitch of the electrodes may depend on the system design requirements.

A capacitive fingerprint sensor array includes capacitive sense elements that may produce signals suitable for detecting, determining positions of, tracking, and/or imaging the features of the fingerprint on or near a sensor surface. A capacitive sense element may comprise an electrode, a discrete unit of electrodes, or an intersection of electrodes from which a measurement or signal may be obtained that is separate and distinct from measurements/signals obtained from other sense elements in the capacitive sensor array. A unit cell refers to a discrete area of the capacitive sensor array in which every point within the unit cell is closer to one sense element than to an adjacent sense element.

Capacitive fingerprint sensors function by measuring the capacitance of a capacitive sense element and detecting a change in capacitance indicating a presence or absence of fingerprint features. Fingerprint features may include, but are not be limited to, valleys and ridges forming arches, loops, and whorls. For example, when a fingerprint ridge comes into contact with or is in close proximity to a sense element, the capacitance change caused by the fingerprint ridge may be detected. The change in capacitance that may be measured in response to a fingerprint feature is around 0.05 fF. The capacitance change of the sense elements may be measured by electrical circuitry that converts the capacitances measured from the capacitive sense elements into digital values from which fingerprint data may be derived. As used herein, "fingerprint data" refers to a set of data values that represent a fingerprint in digital format. In some embodiments, fingerprint data may be a dataset that visually represents the valleys and ridges of a fingerprint with their arches, loops, and whorls. In other embodiments, fingerprint data may digitally represent a fingerprint in a non-visual form.

A fingerprint sensor system as illustrated in FIG. 4 may include certain features to enable accurate imaging of a fingerprint. In an embodiment, the pitch of row electrodes and column electrodes may be small enough such that multiple rows or columns may be disposed within a valley or along a ridge of a fingerprint feature when a finger is in contact with, or in close proximity to, a fingerprint sensor surface. In some embodiments, the pitch may be selected such that each fingerprint feature may be detected by a minimum number of capacitive sense elements (e.g., at least three capacitive sense elements). In various embodiments, the pitch of the capacitive sense elements may be less than 100 µm.

The thickness of an overlay disposed over the sensor surface may affect the change in measured capacitance of a capacitive sense element in response to a proximate fingerprint feature. Overlays which enable accurate imaging of a fingerprint may typically be less than 150 µm in thickness. A thicker overlay may reduce the change in measured capacitance of a capacitive sense element in response to a proximate fingerprint feature, which may obscure the fingerprint details.

Anisotropic Conductive Material

An overlay disposed on the sensor surface may typically be made of an isotropic conductive material. In other words, the conductivity of the material is substantially the same in all directions. In an embodiment, the overlay may be made of an anisotropic conductive material. Anisotropic conductive material may be substantially more conductive in one direction, such as a direction orthogonal to a fingerprint sensor surface, than in other directions. The effect of anisotropic conductive material on fingerprint sensing will be discussed further below.

Figures 5A, 5B, 5C:
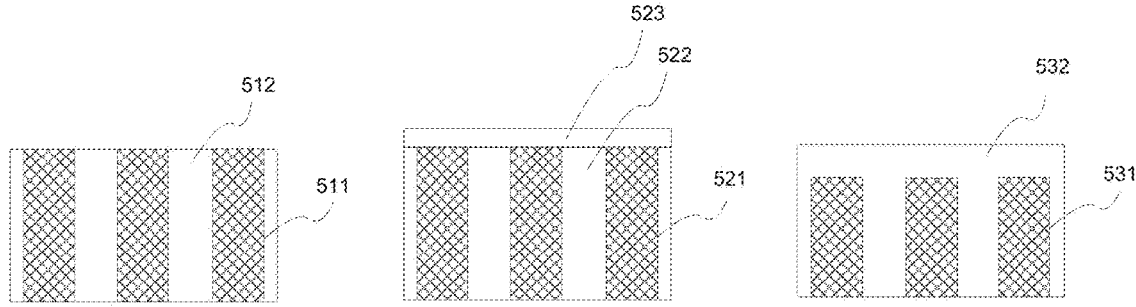
FIGS. 5A-5C illustrate a material with pillars that are fabricated in the material in one direction according to various embodiments.

FIGS. 5A-5C illustrate one method of fabricating anisotropic conductive material by fabricating conductive pathways, or "pillars," in a material. Pillars may be fabricated by methods including, but not limited to, drilling, piercing, or perforating a material, including laser-assisted methods. The pillars may be areas within the material that are devoid of the material. The pillars may be fully or partially filled with air, dielectric material, or a conductive material. Pillars may be filled with material by methods including, but not limited to, pasting material in the pillars, electro-plating the pillars, or depositing micro-particles. The pillars may be fully or partially filled. The pillars may be coated with a conductive material. The conductive material may comprise copper or Indium tin oxide.

FIG. 5A illustrates a material 512 with pillars 511 that are fabricated completely through material 512 from one surface of the material in one direction. Through-material pillars may be preferable in some embodiments because they may provide uniform depth and conductivity because the through-material pillars perfectly match the thickness of the material they penetrate. As described further below, uniform depth and conductivity may improve fingerprint sensing through the anisotropic conductive material. Material fabricated with through-material pillars may be ground to reduce the material to a desired thickness. After fabricating the pillars, one or both of the surfaces of material with though-material pillars may be covered by a thin layer of a cover material to provide a surface to receive a fingerprint. The cover material would be of controlled thickness across the surface of the anisotropic conductive material. FIG. 5B illustrates a material 522 with pillars 521 that are fabricated completely through material 522, and with a cover material 523. FIG. 5C illustrates a material 532 with pillars 531 that are fabricated completely through material 532, and with a cover material 533.

FIG. 5B illustrates a material 522 with pillars 521 that are fabricated partly through material 522. Pillars fabricated partially through a material may be called "blind pillars." Blind pillars may eliminate the need to attach an intermediate material to provide a surface to receive a fingerprint. Material fabricated with blind pillars may be ground to reduce the material to a desired thickness.

Figure 6A:
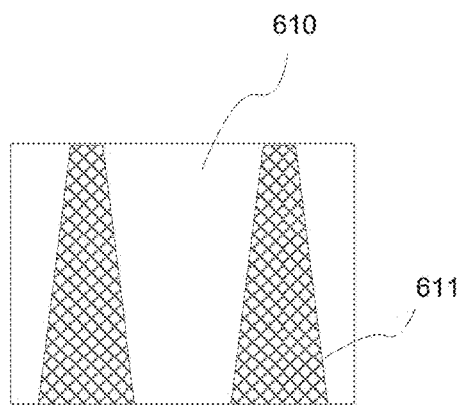
FIGS. 6A-6B illustrate a material with pillars fabricated in the material in shapes according to various embodiments.
Figure 6B:
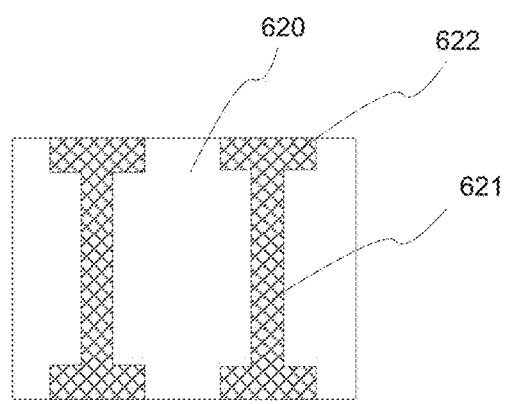

Pillars may be fabricated in different shapes. FIGS. 5A-5C, illustrate pillars 511, 521, and 531 formed in the shape of a cylinder. FIG. 6A illustrates a material 610 with pillars 611 formed in the shape of a cone. FIG. 6B illustrates a material 620 with pillars 621 formed in the shape of a cylinder with plates 622 at each end. A cylinder with one or two plates 622 may have smaller capacitive coupling to neighboring pillars than cylinders, while providing large areas at each surface for strong coupling to a fingerprint and a fingerprint sensor. In other embodiments, the pillars may be formed in other shapes.

Figure 7A:
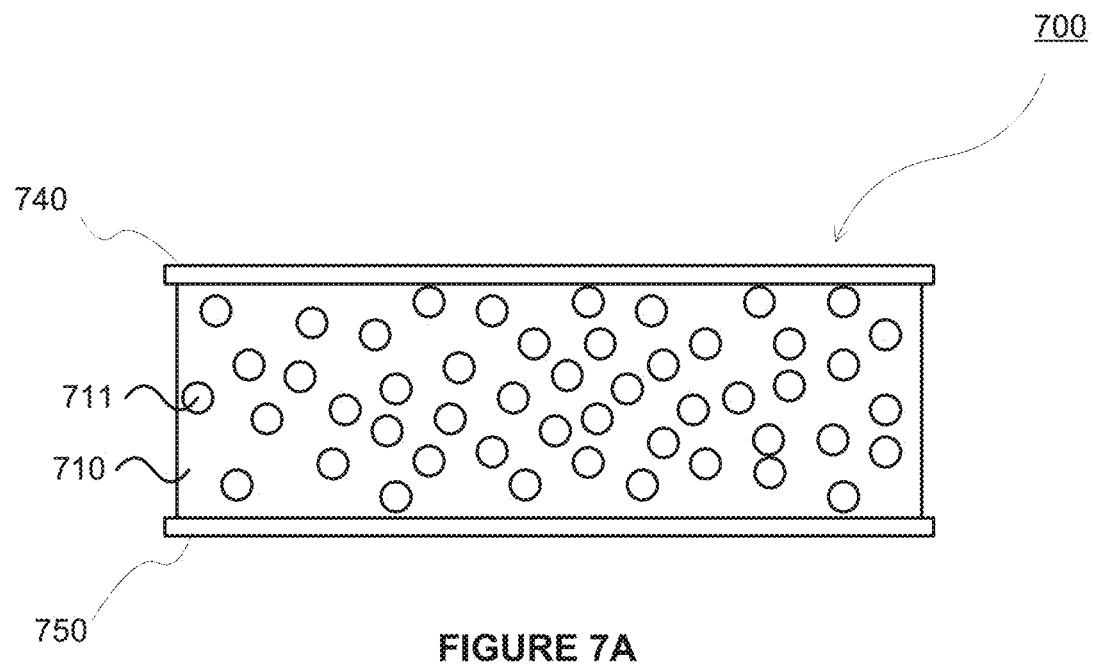
FIGS. 7A-7B illustrate a material in which conductive elements have been incorporated into the material according to various embodiments.
Figure 7B:
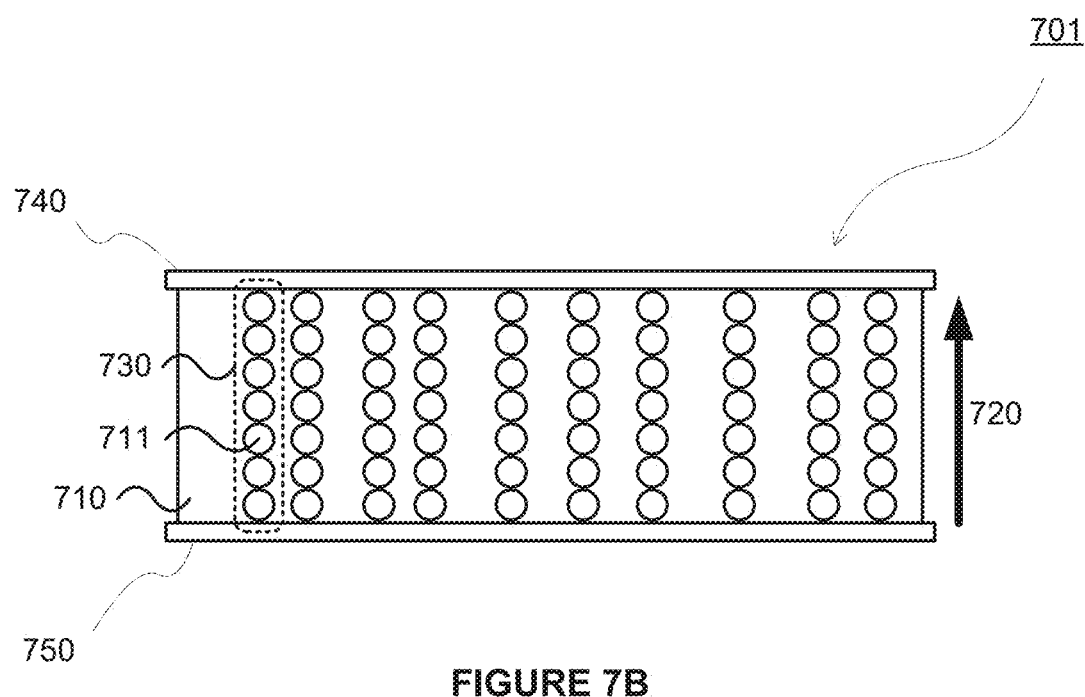

FIGS. 7A and 7B illustrate another method to fabricate anisotropic conductive material by incorporating conductive elements in a material. FIG. 7A illustrates a material 710 in which conductive elements 711 have been randomly incorporated. In an embodiment, the embedded conductive particles may be less than 20 µm in diameter. FIG. 7B illustrates material 710 after an electric or magnetic field force 720 has been applied across material 710 during a manufacturing step. Electric or magnetic field 720 may be applied in a direction substantially orthogonal to material surface 740 and material surface 750. The direction of applied electric or magnetic field 720 is indicated by the arrow. The electric or magnetic field force may align conductive elements 711 in the direction of the applied electric or magnetic field 720, thus forming the equivalent of "pillars" 730 aligned in the direction of the applied electric or magnetic field 720. Thus, material 710 will have increased conductivity in the alignment direction of pillars 730. In a specific embodiment, the conductive elements are ferro-electric conductive particles and a magnetic field has been applied. In other embodiments, other conductive elements 711 such as conductive filaments may be used. In other embodiments, conductive elements 711 may be aligned to form the equivalent of pillars 730 by applying an electric field across material 710 in a direction substantially orthogonal to material surface 740 and material surface 750. In still other embodiments, conductive elements 711 may be aligned to form the equivalent of pillars 730 by applying pressure across material 710 in a direction substantially orthogonal to material surface 740 and material surface 750.

Figure 8A:
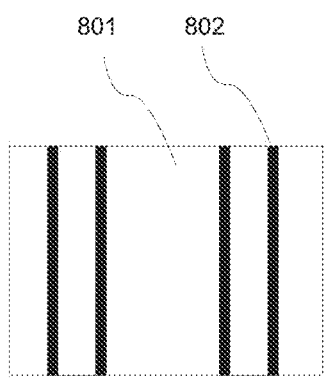
FIGS. 8A-8C illustrate a material in which conductive elements have been incorporated into the material according to various embodiments.
Figure 8B:
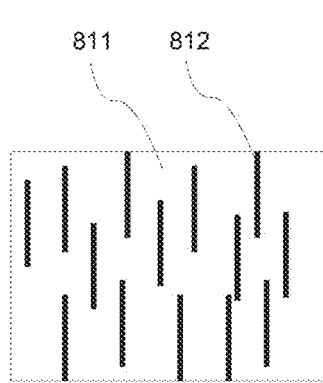
Figure 8C:
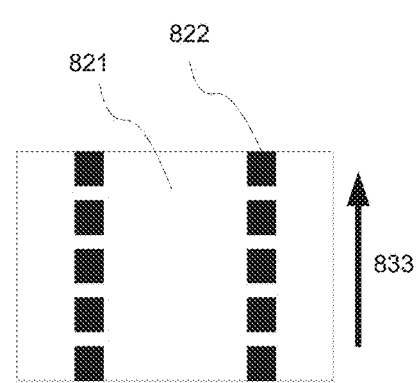

FIGS. 8A-8B illustrate another method to fabricate anisotropic conductive material by incorporating conductive elements in a material. FIG. 8A illustrates a material 801 in which conductive elements 802 have been fabricated in a material such that the conductive elements are aligned from one surface to a second surface of the material and reach through the material in one direction, forming "pillars." FIG. 8B illustrates a material 811 in which conductive elements 812 have been fabricated in a material such that the conductive elements are aligned from one surface of the material to a second surface of the material in one direction but do not reach through the material, forming "pillars." FIG. 8C illustrates a material 821 in which conductive elements 822 have been fabricated in a material such that the conductive elements are aligned in direction 833 from one surface of the material, and where the distance between the conductive elements in direction 833 is smaller than the distance between the conductive elements in other directions, forming "pillars." Thus, material 801, 811, and 821 will have increased conductivity in the alignment direction 833 of the pillars. The conductive elements of FIGS. 8A-8C may comprise, but are not limited to, nano-wires, flakes, microparticles, or bars. The conductive elements illustrated in FIGS. 8A-8C may comprise conductive elements which are the same or similar to those disclosed in FIGS. 5A-5C, 6A-6B, and 7A-7B.

Anisotropic conductive material may be fabricated with rigid materials including, but not limited to, glass, ceramic, or plastic. Anisotropic conductive material may be fabricated with non-rigid materials including, but not limited to, film or fabric.

Anisotropic Conductive Material and Fingerprint Sensing

Figure 9A:
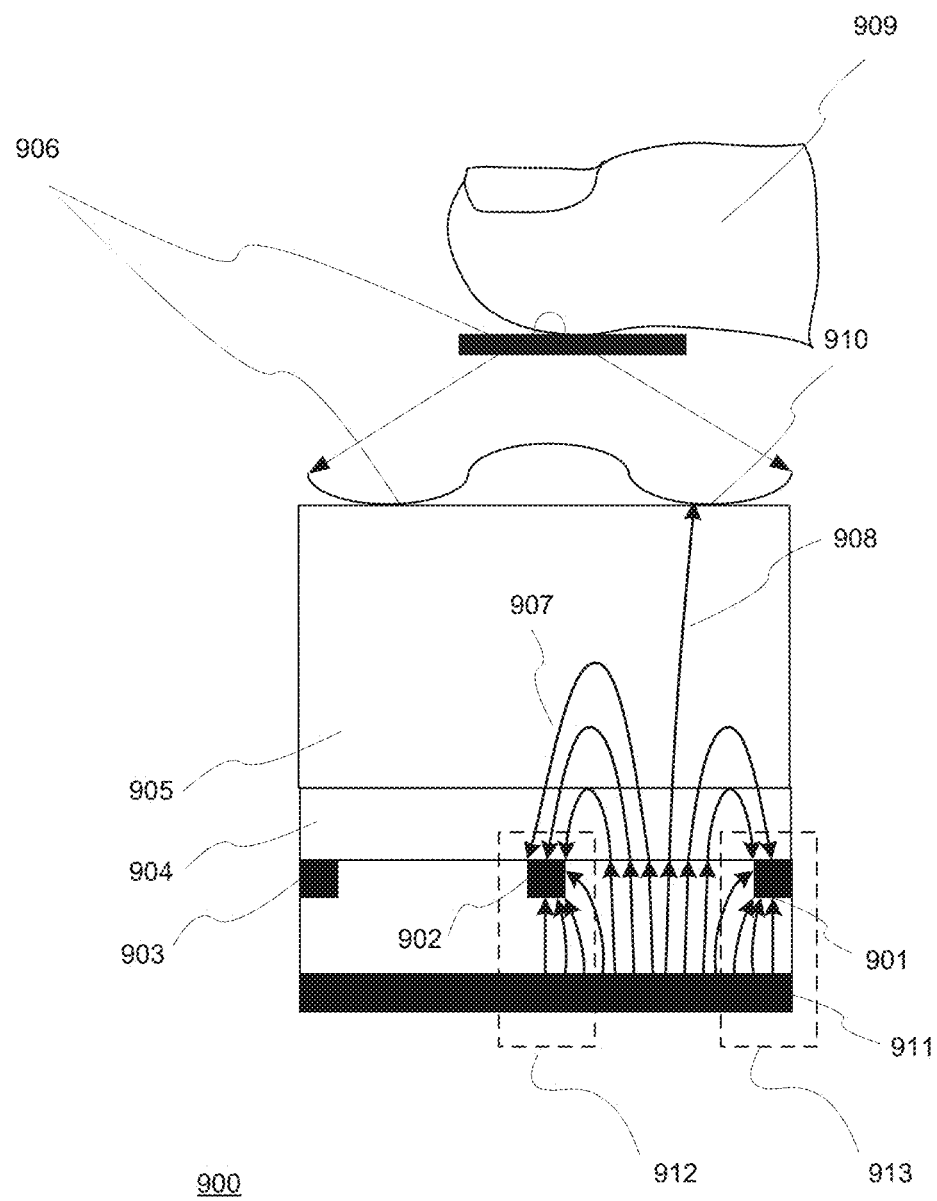
FIGS. 9A-9B illustrates the effect of anisotropic conductive material on the electric field density of a capacitive fingerprint sensor according to various embodiments.
Figure 9B:
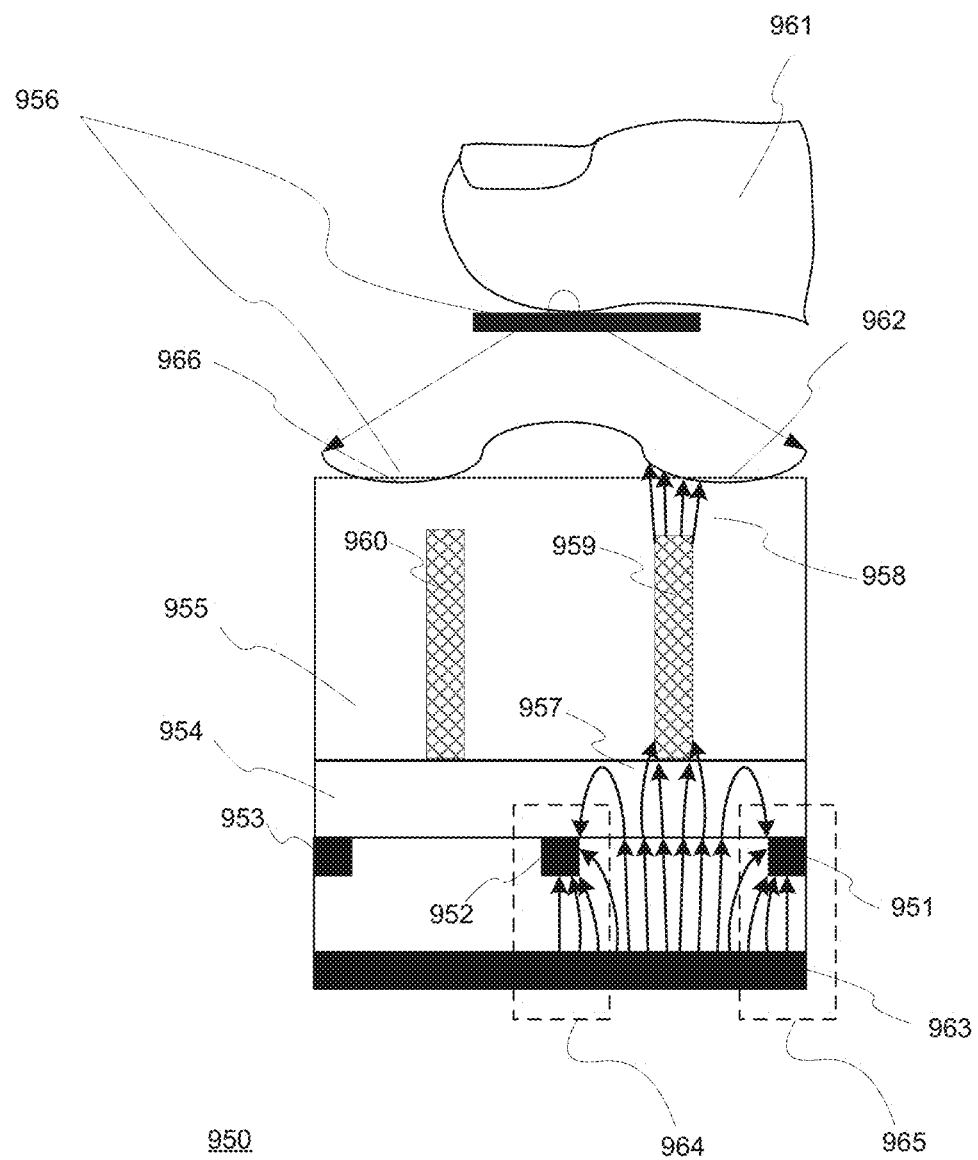

FIGS. 9A and 9B illustrate the effect of pillars in anisotropic conductive material on the electric field density of a capacitive fingerprint sensor which is imaging a fingerprint. FIG. 9A illustrates a mutual capacitance fingerprint sensor 900 comprising Tx electrode 911, Rx electrodes 901, 902, and 903, sensor surface 904, and overlay material 905. In this example, a sense element comprises the intersection of Tx electrode 911 and an Rx electrode 901, 902, or 903. Sense element 912 comprises the intersection of Tx electrode 911 and Rx electrode 902; sense element 913 comprises the intersection of Tx electrode 911 and Rx electrode 901. In this example, Rx electrodes 901, 902, and 903 correspond to column electrodes 404 in FIG. 4, and Tx electrode 911 corresponds to column electrodes 406 in FIG. 4. Mutual capacitance fingerprint sensor 900 measures the change in mutual capacitance of sense elements 912 or 913 in the presence of finger 909 on a surface 906 of overlay material 905. The magnitude of the decrease in mutual capacitance measured by sense elements 912 and 913 is represented by the number of field lines 907 which couple from Tx electrode 911 to finger 909 instead of coupling to Rx electrodes 901 and 902. In this example, the field lines are an abstraction of the strength of capacitive coupling between sense elements 912 and 913 and finger 909. FIG. 9A illustrates that fingerprint ridge 910 is weakly coupled to sense elements 912 and 913 through material 905, causing a slight decrease in measured mutual capacitance, as represented by the single field line 908 that is shunted away from sense elements 912 and 913 to ridge 910.

FIG. 9B illustrates a mutual capacitance fingerprint sensor 950 comprising Tx electrode 963, Rx electrodes 951, 952, and 953, sensor surface 954, and overlay material 955. In this example, a sense element comprises the intersection of Tx electrode 963 and an Rx electrode 951, 952, or 953. Sense element 964 comprises the intersection of Tx electrode 963 and Rx electrode 952; sense element 964 comprises the intersection of Tx electrode 911 and Rx electrode 951. Overlay material 955 comprises pillars 959 and 960. The magnitude of the decrease in mutual capacitance measure by sense elements 964 and 965 in the presence of finger 961 on a surface 956 of the overlay material is represented by the number of field lines 958 which couple from Tx electrode 963 to finger 961 instead of coupling to Rx electrodes 964 and 965. FIG. 9B illustrates that fingerprint ridge 962 is strongly coupled to sense elements 964 and 965 through pillar 959, causing a decrease in measured mutual capacitance, as represented by the four field lines 958 that are coupled away from sense elements 964 and 965 to ridge 962 through pillar 959. In other words, pillar 959 acts as an electric field guide that increases the capacitive coupling of fingerprint ridge 962 to the sense elements 964 and 965, and increases the change in measured capacitance of sense elements 964 and 965. The increase in the magnitude of the decrease in measured mutual capacitance using material 955 comprising pillars 959 and 960 compared to material 905 without pillars is represented by the increase in the number of field lines 957 that are coupled away from sense elements 964 and 965 to fingerprint ridge 962. In the examples of FIGS. 9A and 9B, the increase using material 955 with pillars 959 and 960 is represented by the four field lines 958 compared to the one field line 908 for material 905 without pillars. It is to be understood that conductively anisotropic material may similarly be used with self-capacitance fingerprint sensors where the increased capacitive coupling of the pillar causes an increase in the measured change in capacitance by sense elements. It is also to be understood that the alignment of pillars 959 and 960 to fingerprint ridges 962 and 966 is exemplary only; pillars may or may not be aligned with fingerprint ridges and/or fingerprint valleys.

Figure 10A:
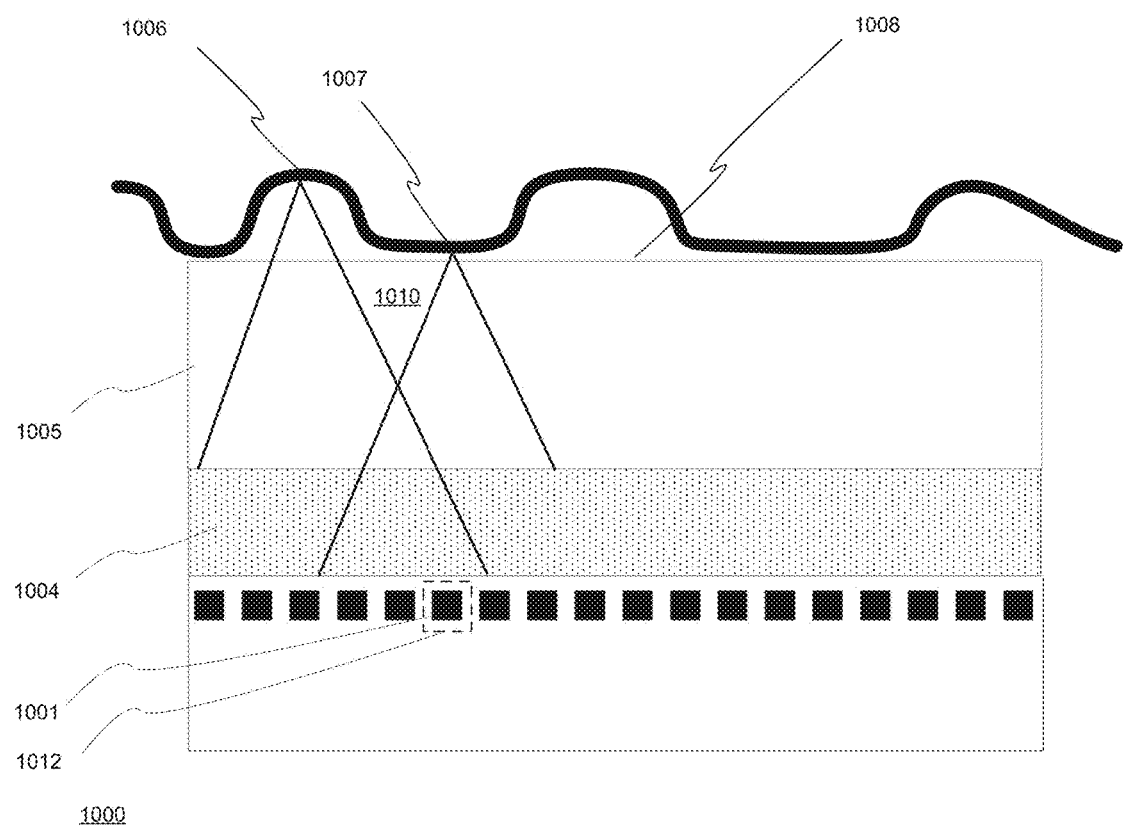
FIGS. 10A-10B illustrate the effect of anisotropic conductive material on the imaging of a fingerprint by a fingerprint sensor according to various embodiments.
Figure 10B:
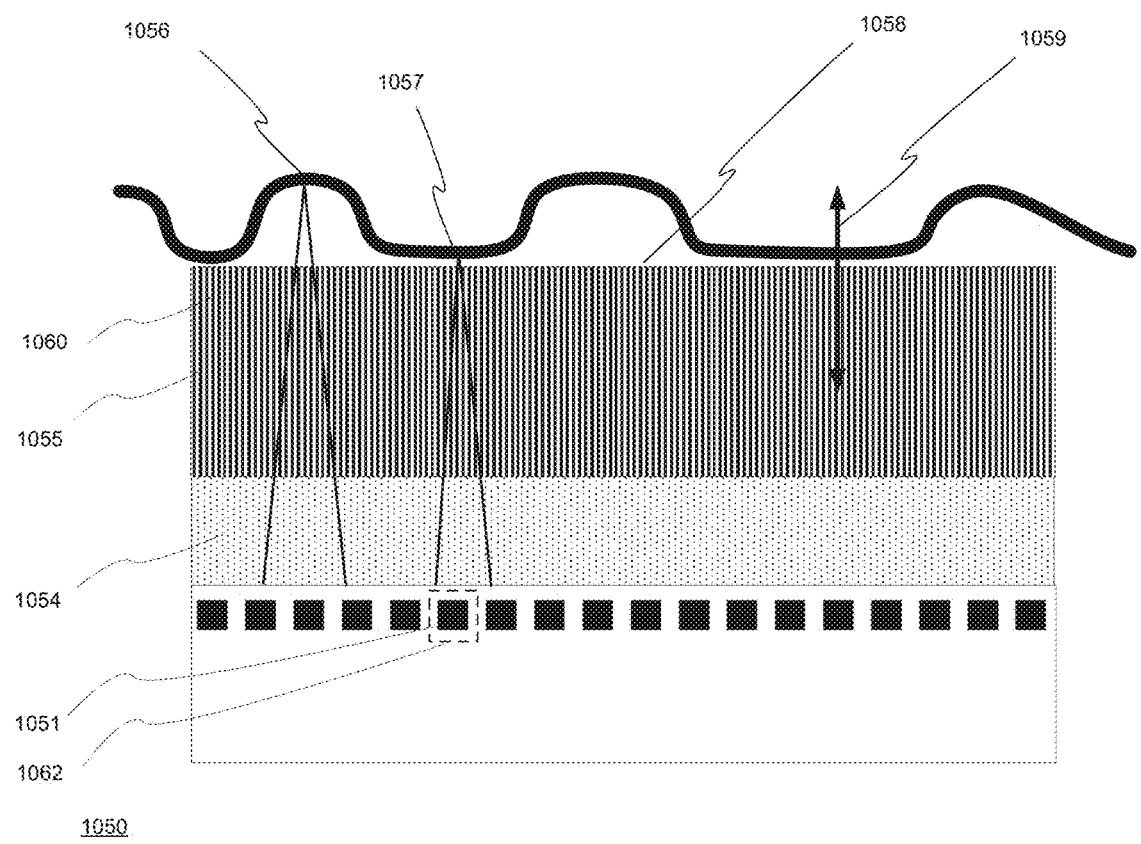

FIGS. 10A and 10B illustrate another example of the effect of anisotropic conductive material on the imaging of a fingerprint by a fingerprint sensor. FIG. 10A illustrates a self capacitance fingerprint sensor 1000 comprising electrode 1001, sensor surface 1004, and overlay material 1005. In this example, sense element 1012 comprises electrode 1001. Self capacitance fingerprint sensor 1000 measures the change in self capacitance of sense element 1012 in the presence of fingerprint feature 1006, corresponding to a fingerprint valley, and fingerprint feature 1007, corresponding to a fingerprint ridge, on surface 1008 of overlay material 1005. Fingerprint features 1006 and 1007 disperse as they capacitively couple through overlay material 1005 to sense element 1012. The dispersion, or "blurring", of fingerprint features 1006 and 1007 through overlay material 1005 is represented by lines 1010. In this example, lines 1010 are an abstraction of the dispersion of fingerprint features 1006 and 1007 through overlay material 1005 to sense elements 1012. FIG. 10A illustrates that dispersion of fingerprint features 1006 and 1007 through overlay material 1005 may enable each fingerprint feature 1006 and 1007 to capacitively couple to multiple sense elements 1012, and also may enable sense element 1012 to capacitively couple to multiple fingerprint features 1006 and 1007. Increasing the number of fingerprint features 1006 and 1007 that capacitively couple to a sense element 1012, or increasing the number of sense elements 1012 that capacitively couple to each of fingerprint features 1006 and 1007, reduces the accuracy of fingerprint imaging by sense element 1012 and, therefore, by fingerprint sensor 1000.

FIG. 10B illustrates a self capacitance fingerprint sensor 1050 comprising electrode 1051, sensor surface 1054, and anisotropic conductive material 1055. The direction of increased conductivity in anisotropic conductive material 1055 is represented by arrow 1059. In this example, sense element 1062 comprises electrode 1051. Self capacitance fingerprint sensor 1050 measures the change in self capacitance of sense element 1062 in the presence of fingerprint features 1056 and 1057 on surface 1058 of anisotropic conductive material 1055. Fingerprint features 1056 and 1057 may disperse as they capacitively couple through anisotropic conductive material 1055 to sense element 1062. The dispersion of fingerprint features 1056 and 1057 through anisotropic conductive material 1055 is represented by lines 1060. FIG. 10B illustrates that dispersion of fingerprint features 1056 and 1057 through anisotropic conductive material 1055 is less than dispersion of dispersion of fingerprint features 1006 and 1007 through overlay material

1005 as illustrated in FIG. 10A. The pillars (not shown) of anisotropic conductive material 1055 may act like electric field guides that decrease the dispersion of the fingerprint features as sensed by sense element 1062. Reducing the dispersion of fingerprint features 1056 and 1057 may enable each fingerprint feature 1056 and 1057 to capacitively couple to fewer sense elements 1062, and may enable each sense element 1062 to capacitively couple to fewer fingerprint features 1056 and 1057, thus increasing the accuracy of fingerprint imaging by fingerprint sensor 1050. It is to be understood that conductively anisotropic material may similarly be used with mutual capacitance fingerprint sensors where the reduced dispersion of fingerprint features may also enable each fingerprint feature to capacitively couple to fewer sense elements 1062, and may enable each sense element to capacitively couple to fewer fingerprint features, thus increasing the accuracy of fingerprint imaging by the mutual fingerprint sensor.

Figure 11A:
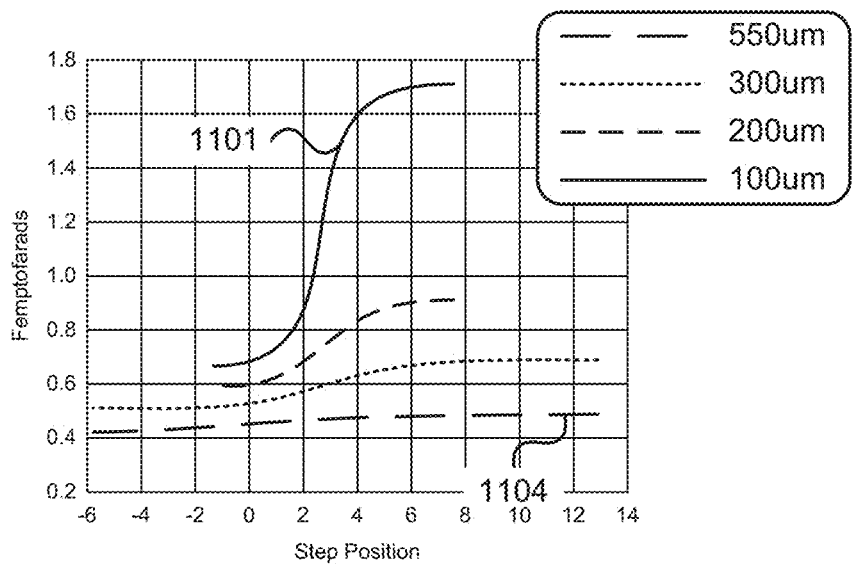
FIGS. 11A-11B illustrate measured capacitance according to various embodiments.
Figure 11B:
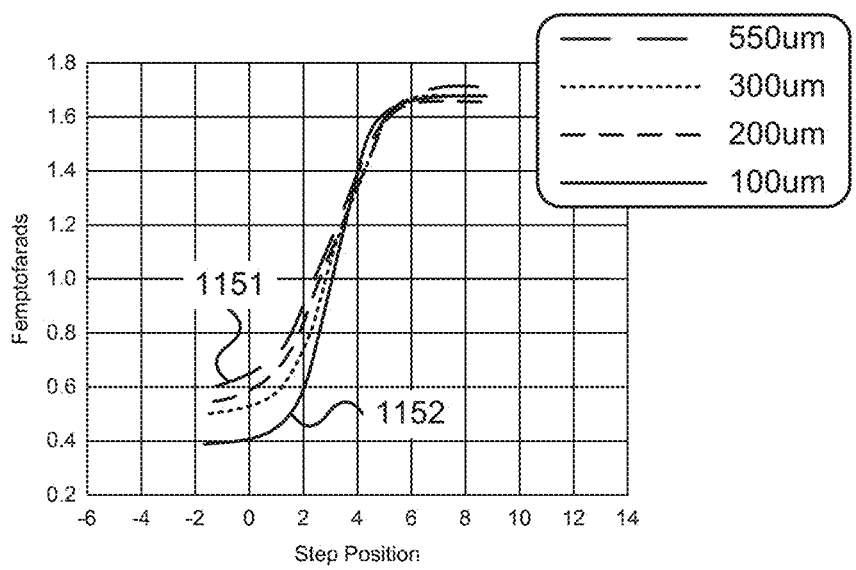

FIGS. 11A and 11B further illustrate an example of the effect of anisotropic conductive material on the imaging of a finger by a fingerprint sensor using self-capacitance. In the graphs of FIGS. 11A and 11B, the y-axes represent the measured capacitance in femtofarads (fF). Position 0 on the x-axes represents a transition between a valley of an imaged fingerprint and a ridge. The graphs illustrate the change in measured capacitance between a fingerprint valley and a fingerprint ridge using overlay materials of varying thickness (100 μm-550 μm) which are in contact with both the fingerprint and the fingerprint sensor surface. FIG. 11A illustrates the change in measured capacitance using overly material without pillars. Line 1101 indicates the measured capacitance of an imaged fingerprint where the overlay material is 100 μm thick. At x-axis position −2, corresponding to a valley, the measured capacitance on line 1101 is approximately 0.6 fF. At x-axis position 6, corresponding to a ridge, the measured capacitance of line 1101 is approximately 1.7 fF. Thus, the measured change in capacitance of line 1101 is approximately 1.1 fF. Line 1104 indicates the measured capacitance of an imaged fingerprint where the overlay material is 550 μm. At x-axis position −2, corresponding to a valley, the measured capacitance of line 1104 is approximately 0.35 fF. At x-axis position 6, corresponding to a ridge, the measured capacitance of line 1104 is approximately 0.40 fF. Thus, the measured change in capacitance of line 1104 is approximately 0.05 fF.

FIG. 11B illustrates an example of the change in measured capacitance using overlay material with pillars. Line 1151 indicates the measured capacitance of an imaged fingerprint where the overlay material with pillars is 100 μm. At x-axis position −2, corresponding to a valley, the measured capacitance of line 1151 is approximately 0.4 fF. At x-axis position 6, corresponding to a ridge, the measured capacitance of line 1151 is approximately 1.7 fF. Thus, the measured change in capacitance of line 1151 is approximately 1.3 fF. Line 1154 indicates the measured capacitance of an imaged fingerprint where the overlay material with pillars is 550 μm. At x-axis position −2, corresponding to a valley, the measured capacitance of line 1154 is approximately 0.6 fF. At x-axis position 6, corresponding to a ridge, the measured capacitance of line 1114 is approximately 1.7 fF. Thus, the measured change in capacitance is approximately 1.1 fF.

As shown in FIGS. 11A and 11B, the measured change in capacitance using conventional material (without pillars) decreases significantly as the overlay thickness increases. The measured change in capacitance does not decrease as much using material with pillars as the overlay thickness increases. In other words, the pillars act like an electric field guide that increases the capacitive coupling of fingerprint features to the sense elements, reducing the decrease in the measured change in capacitance due to proximity of fingerprint features such as ridges through a thick overlay. The use of an overlay with pillars thus substantially increases the thickness of the overlay material through which the fingerprint sensor may accurately image a fingerprint.

The accuracy of fingerprint imaging increases as the number of capacitive sense elements that may detect each fingerprint features increases. Increasing the density of pillars relative to capacitive sense elements increases the number of sense elements that may couple to each fingerprint feature strongly enough to detect the fingerprint feature. Increasing the density of pillars relative to capacitive sense elements also decreases the effect of the alignment of pillars to sense elements. Thus, increasing the density of pillars increases the accuracy of fingerprint imaging through an overlay, increasing the density of pillars also increases the thickness of an overlay that may enable accurate imaging of a fingerprint.

Decreasing the density of pillars relative to capacitive sense elements increases the effect of the alignment of pillars to sense elements. In an embodiment where there is one pillar for each capacitance sense element, alignment of each pillar to a sense element increases the coupling of fingerprint features to each sense element, thus increasing the accuracy of fingerprint imaging. In a specific embodiment where there is one pillar for each capacitance sense element, centering the pillars in each unit cell provides the most effective conductive coupling and the most accurate fingerprint imaging.

In an embodiment the e there is less than one pillar for each capacitance sense element, accuracy of fingerprint imaging through an overlay is less than embodiments with one or more pillars for each capacitance sense element. However, accuracy of fingerprint imaging through an overlay with less than one pillar for each capacitance sense element is greater than accuracy of fingerprint imaging through an overlay without pillars.

In an embodiment, the pillars may be in direct physical contact with the sense elements. In other embodiments, for ease of fabrication, the pillars may not be in direct physical contact with the sense elements. In an embodiment where pillars are in direct physical contact with to the sense elements, accuracy of fingerprint imaging through an overlay is greater than embodiments where pillars are not in direct physical contact with the sense elements. However, accuracy of fingerprint imaging through an overlay where pillars are not in direct physical contact with the sense elements is greater than accuracy of fingerprint imaging through an overlay without pillars.

FIGS. 12A-D illustrate embodiments where pillars are arranged symmetrically around an axis in the direction of the pillars with a uniform density of one pillar per mutual capacitance sense element. FIGS. 12A-D illustrate four symmetric arrangements of pillars 1201 with a uniform density of one pillar per mutual capacitance sense element 1203, sense element 1203 comprising the intersection of Rx electrode 1202 and Tx electrode 1204.

Figure 12A:
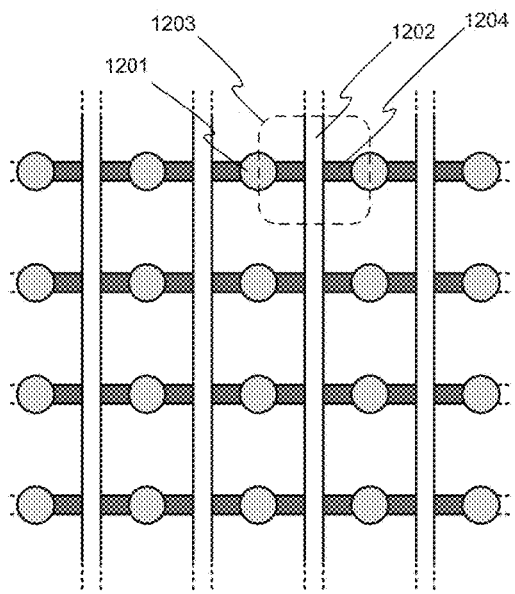
FIGS. 12A-12I illustrate arrangements of pillars according to various embodiments.
Figure 12B:
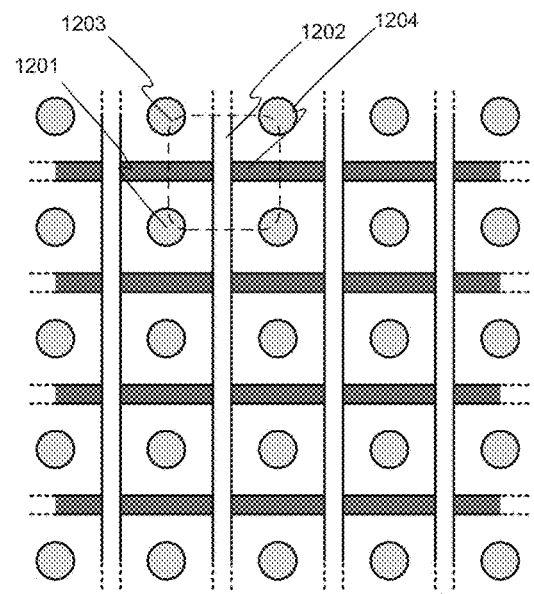
Figure 12C:
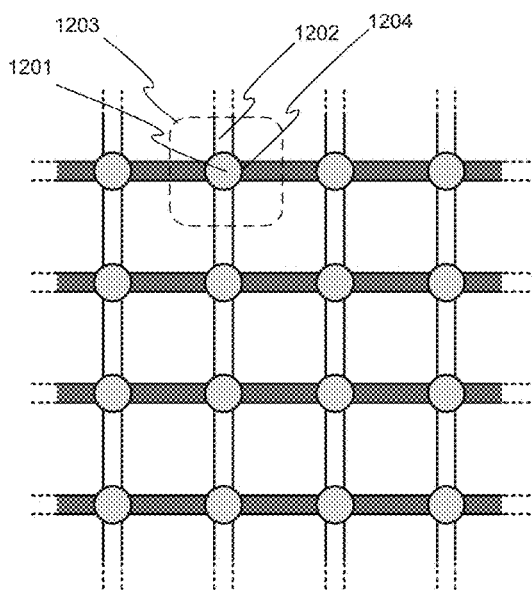
Figure 12D:
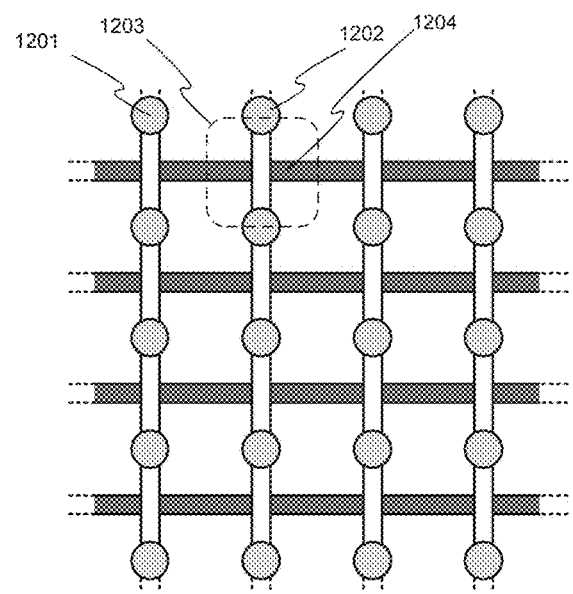
Figure 12E:
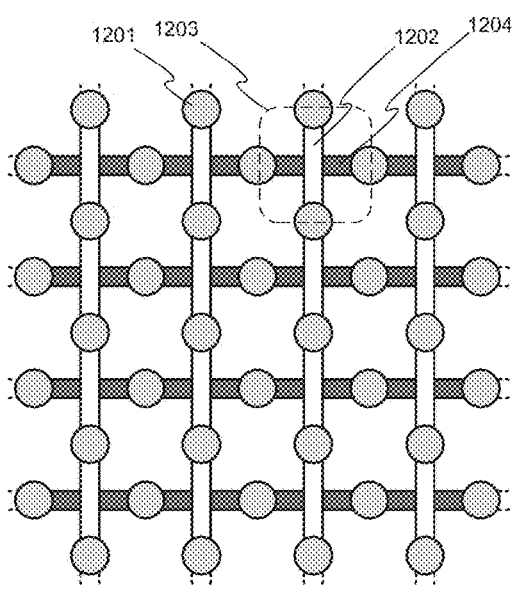
Figure 12F:
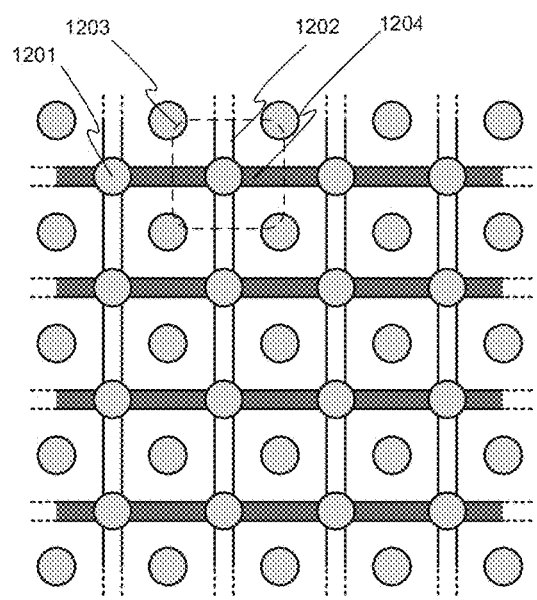

FIGS. 12E-F illustrate embodiments where pillars are arranged symmetrically around an axis in the direction of the pillars with a uniform density of two pillars per mutual capacitance sense element. FIGS. 12E-F illustrate two symmetric arrangements of pillars 1201 with a uniform density of two pillars 1201 per mutual capacitance sense element 1203, sense element 1203 comprising the intersection of Rx electrode 1202 and Tx electrode 1204.

Figure 12G:
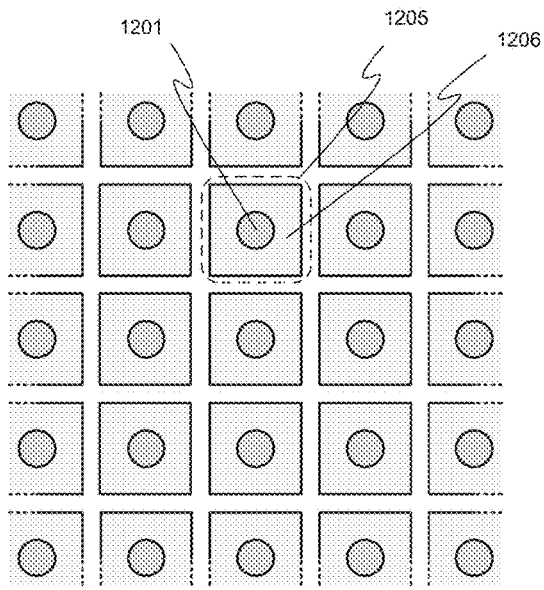
Figure 12H:
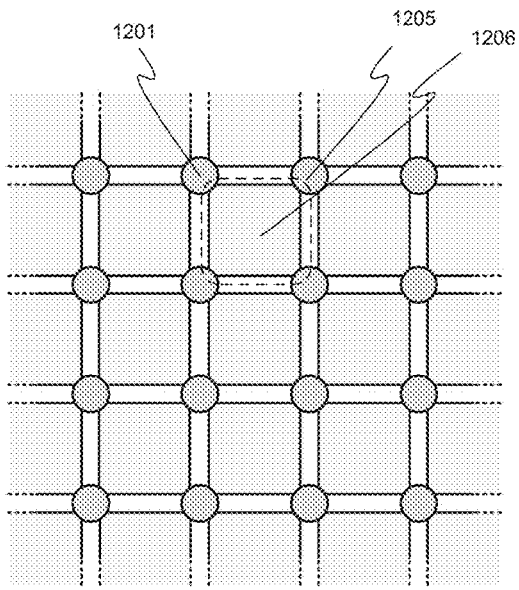

FIGS. 12G-H illustrate embodiments where pillars are arranged symmetrically around an axis in the direction of the pillars with a uniform density of one pillar per self capacitance sense element. FIGS. 12G-H illustrate two symmetric arrangements of pillars 1201 with a uniform density of one pillar per self capacitance sense element 1205, sense element 1205 comprising electrode 1206.

Figure 12I:
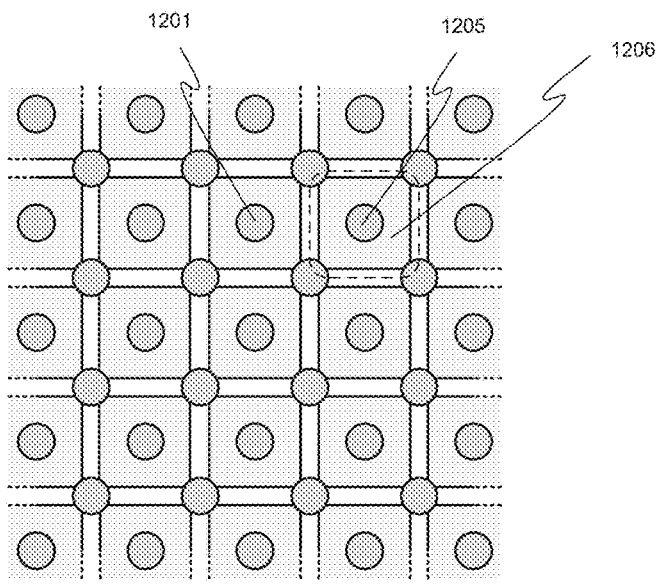

FIG. 12I illustrates an embodiment where pillars are arranged symmetrically around an axis in the direction of the pillars with a uniform density of two pillars per self capacitance sense element. FIG. 12I illustrates a symmetric arrangement of pillars 1201 with a uniform density of two pillars per self capacitance sense element 1205, sense element 1205 comprising electrode 1206.

It is to be understood that anisotropic material may comprise pillars with a relative density of more than two pillars per capacitive sense element for both mutual capacitance and self capacitance.

Figure 13:
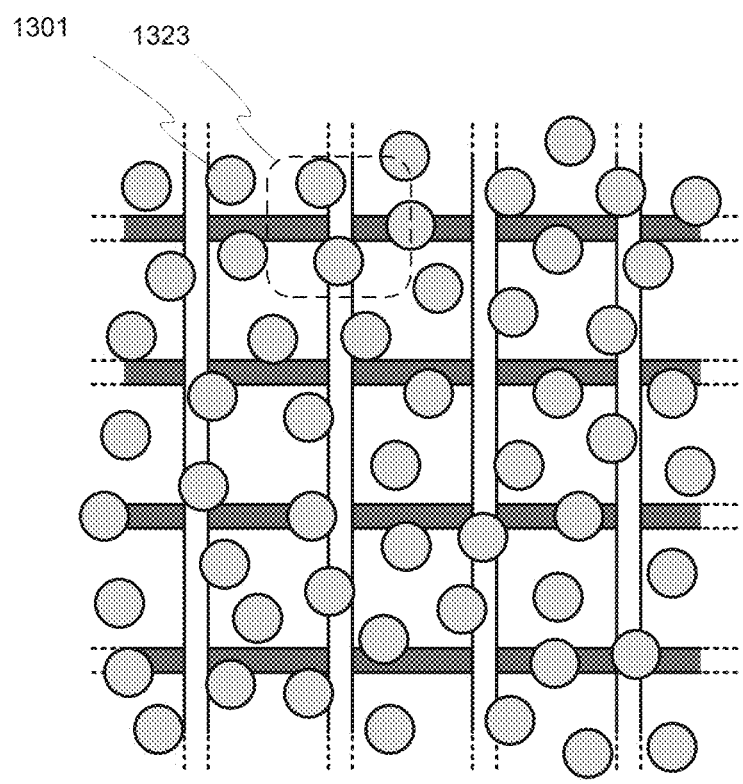
FIG. 13 illustrates an arrangement of pillars according to an embodiment.

FIG. 13 illustrate an embodiment where pillars 1301 are arranged randomly and asymmetrically around an axis in the direction of the pillars with a uniform density of one pillar per mutual capacitance sense element 1302. An asymmetric arrangement of pillars may be desirable for ease of fabrication. A random arrangement of pillars may also be desirable for ease of fabrication. An asymmetric arrangement of pillars may be desirable in flexible material, to allow the material to flex yet still provide effective conductive coupling through the pillars. When the pillars have an asymmetric arrangement, the fingerprint sensor may more accurately image a fingerprint when the asymmetric pillars have a uniform distribution density. When the pillars have an asymmetric arrangement, increasing the density of pillars relative to capacitive sense elements increases the number of sense elements that may couple to each fingerprint feature strongly enough to detect the fingerprint feature. Thus, increasing the density of asymmetrically arranged pillars increases the accuracy of fingerprint imaging.

It is to be understood that a self capacitance fingerprint sensor may also more accurately image a fingerprint when asymmetric pillars have a uniform distribution density per self capacitance sense element, and that increasing the density of asymmetrically arranged pillars increases the accuracy of fingerprint imaging using self capacitance sense elements.

Figures 14A, 14B:
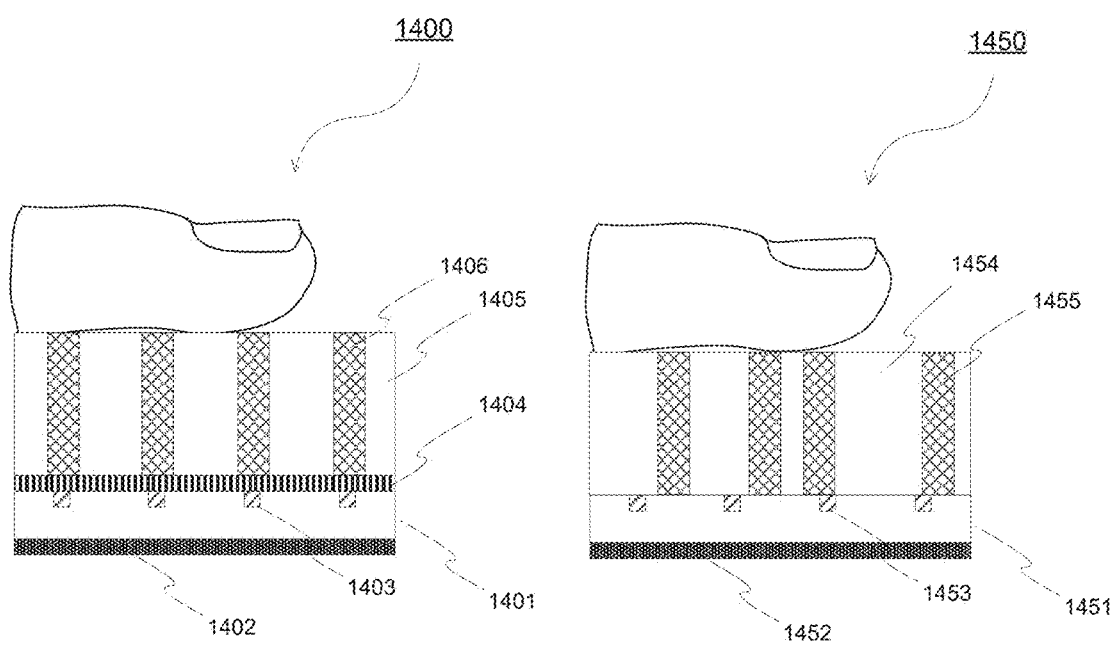
FIG. 14A-14B illustrate a fingerprint sensor structure according to various embodiments.

FIG. 14A illustrates a fingerprint sensor structure 1400 comprising a mutual capacitance fingerprint sensor 1401 with Tx electrodes 1402 and Rx electrodes 1403, intermediate material 1404, and overlay 1405. Intermediate material 1404 may be an adhesive or color-matching paint. Overlay 1405 comprises pillars 1406. In this embodiment, pillars 1406 are symmetrically arranged around an axis in the direction of the pillars, with a density of one pillar per mutual capacitance sense elements and pillars 1406 are aligned to the sense elements. It is to be understood that overlay 1405 may be fabricated with pillars 1406 in other arrangements. In the embodiment comprising an intermediate material 1404, it is to be understood that the intermediate material must allow adequate coupling between the fingerprint and the sense elements through the intermediate material and the overlay. In a specific embodiment, intermediate material 1404 may also comprise pillars; in various embodiments, overlay 1405 and intermediate material 1404 may be fabricated with the same or different arrangements of pillars.

FIG. 14B illustrates a fingerprint sensor structure 1450 comprising a mutual capacitance fingerprint sensor 1451 with Tx electrodes 1452 and Rx electrodes 1453. Overlay 1454 comprises pillars 1455. In this embodiment, the pillars are randomly and asymmetrically arranged around an axis in the direction of the pillars, with a density of one pillar per mutual capacitance sense elements and the pillars 1455 are not aligned to the sense elements, Rx electrodes 1453. This embodiment does not include an intermediate material.

Referring back to FIG. 5B, a fingerprint sensor structure may comprise an overlay comprising material 522, pillars 521, and cover layer 523. In the embodiment comprising an cover layer 523, it is to be understood that the cover layer 523 must allow adequate coupling between the fingerprint and the sense elements through cover layer 523 and material 522. In a specific embodiment, cover layer 523 may also comprise pillars; in various embodiments, material 522 and cover layer 523 may be fabricated with the same or different arrangements of pillars.

Figure 15:
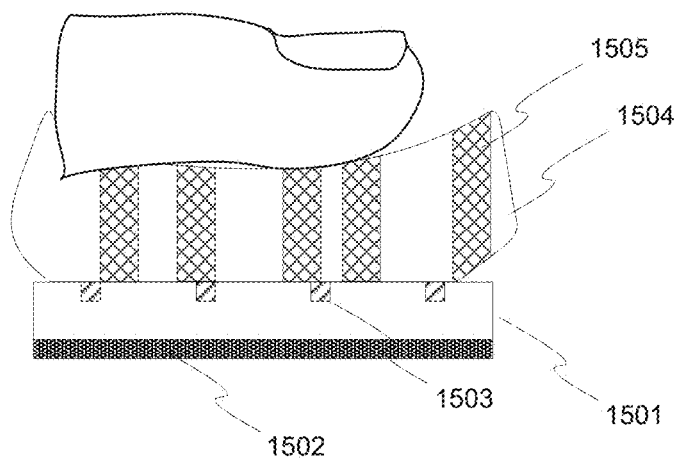
FIG. 15 illustrates a system fingerprint sensor structure according to an embodiment.

A fingerprint sensor overlay comprising anisotropic conductive material as described in reference to FIGS. 12A-14B may be fabricated with rigid materials including, but not limited to, glass, ceramic, or plastic, or may be fabricated with flexible materials including, but not limited to, film or fabric. A fingerprint sensor overlay comprising anisotropic conductive material as described above may be fabricated such that a surface may be able to conform to the curvature of a finger; in a specific embodiment the surface is not deformed by the fingerprint ridge/valley structure. A fingerprint sensor overlay comprising anisotropic conductive material that is flexible and/or has a surface that is conformable may be desirable for ease of fabrication or ease of use. FIG. 15 illustrates a fingerprint structure 1500 comprising a mutual capacitance fingerprint sensor 1501 with Tx electrodes 1502 and Rx electrodes 1503. In this embodiment, overlay 1504 comprises flexible material with pillars 1505 arranged randomly and asymmetrically around an axis in the direction of the pillars with a density of one pillar per mutual capacitance sense elements. In another embodiment, the overlay may comprise a layer which is rigid and a cover layer which is flexible and/or has a surface which may be conformable.

It is to be understood that these embodiments are exemplary only. Other embodiments may include self-capacitance sense elements, more than one intermediate layer, more than one layer of anisotropic conductive material comprising pillars, and material with a conformable surface.

In the above description, numerous details are set forth. It will be apparent, however, to one of ordinary skill in the art having the benefit of this disclosure, that embodiments of the present invention may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those in the data processing arts to most effectively convey the substance of their work to others skilled in the art. An algorithm is here and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "integrating," "comparing," "balancing," "measuring," "performing," "accumulating," "controlling," "converting," "accumulating," "sampling," "storing," "coupling," "varying," "buffering," "applying," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Embodiments described herein may also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer-readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory, or any type of media suitable for storing electronic instructions. The term "computer-readable storage medium" should be taken to include a single medium or multiple media (e.g., a centralized or distributed database and/or associated caches and servers) that store one or more sets of instructions. The term "computer-readable medium" shall also be taken to include any medium that is capable of storing, encoding or carrying a set of instructions for execution by the machine and that causes the machine to perform any one or more of the methodologies of the present embodiments. The term "computer-readable storage medium" shall accordingly be taken to include, but not be limited to, solid-state memories, optical media, magnetic media, any medium that is capable of storing a set of instructions for execution by the machine and that causes the machine to perform any one or more of the methodologies of the present embodiments.

The algorithms and circuits presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the embodiments as described herein.

The above description sets forth numerous specific details such as examples of specific systems, components, methods and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth above are merely exemplary. Particular implementations may vary from these exemplary details and still be contemplated to be within the scope of the present invention.

It is to be understood that the above description is intended to be illustrative and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method comprising:
    disposing a plurality of conductive elements in a material such that the conductive elements are aligned in a first direction from a first surface of the material to a second surface of the material, wherein a first conductivity in the first direction is greater than a second conductivity in at least one other direction; and
    disposing the material over a sensor surface to form a fingerprint sensor-compatible overlay, wherein the sensor surface corresponds to a plurality of capacitive sense elements of a fingerprint sensor that measures changes in capacitance corresponding to a presence of an object, wherein the fingerprint sensor-compatible overlay comprises a first overlay surface corresponding to the first surface and a second overlay surface corresponding to the second surface, wherein the first conductivity is in a first direction between the first overlay surface and the second overlay surface, and wherein the first overlay surface is adjacent to the sensor surface and the second overlay surface is disposed to receive the object in direct contact with or in close proximity to the second overlay surface such that the first conductivity increases a capacitive coupling of the object to the plurality of capacitive sense elements.

2. The method of claim 1, further comprising aligning the conductive elements in the first direction by applying a field across the material in the first direction.

3. The method of claim 1, wherein the material is flexible.

4. The method of claim 1, wherein the plurality of capacitive sense elements is coupled to a capacitance measurement circuit.

5. An apparatus comprising
    an overlay, comprising:

a first overlay surface disposed adjacent to a sensor surface corresponding to a plurality of capacitive sense elements of a fingerprint sensor that measures changes in capacitance corresponding to fingerprint features; and a second overlay surface, wherein a first conductivity in a first direction between the first overlay surface and the second overlay surface is greater than a second conductivity in at least one other direction, wherein the overlay is configured to:
receive a fingerprint in direct contact with or in close proximity to the second overlay surface; and
increase a capacitive coupling of fingerprint features of the fingerprint to the plurality of capacitive sense elements such that the plurality of capacitive sense elements measure changes in capacitance corresponding to the fingerprint features.

6. The apparatus of claim 5, wherein the overlay is flexible.

7. The apparatus of claim 5, wherein the second overlay surface is configured to conform to a curvature of a finger.

8. The apparatus of claim 5, wherein the first conductivity is substantially constant.

9. The apparatus of claim 5, wherein the overlay comprises conductive pillars comprising conductive elements disposed in a material, and wherein the conductive pillars are aligned in the first direction.

10. The apparatus of claim 9, wherein the conductive pillars are disposed in the material symmetrically around an axis in the first direction.

11. The apparatus of claim 9, wherein the conductive pillars are disposed in the material asymmetrically around an axis in the first direction.

12. The apparatus of claim 11, wherein the conductive pillars are further disposed randomly in the material.

13. The apparatus of claim 5, further comprising:
the fingerprint sensor comprising the plurality of capacitive sense elements disposed adjacent to the sensor surface; and
a processor coupled to the fingerprint sensor, wherein the processor is configured to:
receive measurements of changes in capacitance corresponding to the fingerprint features; and
based on the measurements of changes in capacitance, generate a set of data values that represent the fingerprint in a digital format.

14. The apparatus of claim 5, wherein the overlay comprises a plurality of conductive elements disposed in a material such that conductive elements are aligned in the first direction from a first surface of the material to a second surface of the material.

* * * * *